(12) United States Patent
Axelson, Jr. et al.

(10) Patent No.: US 6,558,391 B2
(45) Date of Patent: May 6, 2003

(54) METHODS AND TOOLS FOR FEMORAL RESECTION IN PRIMARY KNEE SURGERY

(75) Inventors: Stuart L. Axelson, Jr., Succasunna, NJ (US); Michael J. McGovern, Mahwah, NJ (US); Reese K. Meyers, Warsaw, IN (US)

(73) Assignee: Stryker Technologies Corporation, Kalamazoo, MI (US)

( * ) Notice: Subject to any disclaimer, the term of this patent is extended or adjusted under 35 U.S.C. 154(b) by 0 days.

(21) Appl. No.: 09/746,800

(22) Filed: Dec. 23, 2000

(65) Prior Publication Data

US 2003/0018338 A1 Jan. 23, 2003

(51) Int. Cl.⁷ .................................................. A61F 2/38
(52) U.S. Cl. .......................................... 606/88; 606/96
(58) Field of Search ............................... 606/86, 87, 88, 606/89, 96

(56) References Cited

U.S. PATENT DOCUMENTS

| | | | |
|---|---|---|---|
| 4,474,177 A | | 10/1984 | Whiteside |
| 4,487,203 A | | 12/1984 | Androphy |
| 4,502,483 A | | 3/1985 | Lacey |
| 4,524,766 A | | 6/1985 | Petersen |
| 4,567,885 A | | 2/1986 | Androphy |
| 4,718,413 A | | 1/1988 | Johnson |
| 4,892,093 A | * | 1/1990 | Zarnowski et al. ............ 606/82 |
| 5,053,037 A | * | 10/1991 | Lackey ..................... 606/88 X |
| 5,417,695 A | | 5/1995 | Axelson, Jr. |
| 5,454,816 A | * | 10/1995 | Ashby .......................... 606/88 |
| 5,474,559 A | * | 12/1995 | Bertin et al. .................... 606/89 |
| 5,601,563 A | * | 2/1997 | Burke et al. ................... 606/86 |
| 5,624,444 A | * | 4/1997 | Wixon et al. .................. 606/88 |
| 5,653,714 A | * | 8/1997 | Dietz et al. ............... 606/96 X |
| 5,658,292 A | | 8/1997 | Axelson, Jr. |
| 5,743,915 A | | 4/1998 | Bertin et al. |
| 5,749,876 A | * | 5/1998 | Duvillier et al. .......... 606/89 X |
| 5,830,216 A | * | 11/1998 | Insall et al. .................... 606/88 |
| 6,077,270 A | * | 6/2000 | Katz .......................... 606/88 |
| 2001/0001121 A1 | * | 5/2001 | Lombardo et al. ............ 606/89 |

* cited by examiner

*Primary Examiner*—Jeffrey A. Smith
(74) *Attorney, Agent, or Firm*—Lerner, David, Littenberg, Krumholz & Mentlik, LLP

(57) ABSTRACT

Femoral resection tools of the present invention include a posterior condyle alignment guide, an IM rod with an adjustable valgus bushing assembly, left and right external rotation plates, an anterior sizing boom having a stylus and a pair of medial/lateral drill guide assemblies (in one embodiment of the invention the drill guide assemblies are the combination of medial/lateral extension arms and attached (detachable) proximal positioning fixtures; in another embodiment, the proximal positioning fixtures are not part of the drill guide assembly per se), a plurality of self-tapping screws, proximal positioning fixtures (apart from any positioning fixtures that may be integrated into a drill guide assembly), and different size cutting guide blocks, each adapted to fit over the proximal positioning fixtures. Methods for utilizing the aforementioned tools so that five resections can be performed are also described.

32 Claims, 6 Drawing Sheets

METHODS AND TOOLS FOR FEMORAL RESECTION IN PRIMARY KNEE SURGERY

BACKGROUND OF THE INVENTION

1. Field of the Invention

The invention relates to methods and tools used in knee arthroplasty. More particularly, the invention relates to methods and tools used in total knee surgery (primary and revision applications) where an artificial femoral component is installed.

2. Brief Description of the Prior Art

Total knee arthroplasty involves the replacement of portions of the patella, femur and tibia with artificial components. In particular, a proximal portion of the tibia and a distal portion of the femur are cut away (resected) and replaced with artificial components. As used herein, when referring to bones or other body parts, the term "proximal" means closest to the heart and the term "distal" means more distant from the heart. When referring to tools and instruments, the term "proximal" means closest to the practitioner and the term "distal" means distant from the practitioner.

There are several types of knee prostheses known in the art. One type is sometimes referred to as a "resurfacing type". In these prostheses, the articular surface of the distal femur and proximal tibia are "resurfaced" and replaced with respective metal and plastic condylar-type articular bearing components.

The femoral component is a metallic alloy construction (cobalt-chrome alloy or 6A14V titanium alloy) and provides medial and lateral condylar bearing surfaces of multi-radius design of similar shape and geometry as the natural distal femur or femoral-side of the knee joint.

Prior art FIG. 1 is a sectional view of a state of the art femoral component. The interior of the component has five planar fixation surfaces 1–5 and an intramedullary ("IM") stem 6. Prior to installation of the component, the distal femur must be prepared so that it has five fixation surfaces which closely match the interior surfaces of the component and in scenarios where additional stability is desired the IM canal is reamed to accept the IM stem of the component.

More particularly, the distal femur must be resected to have a distal cut surface (corresponding to surface 1 in FIG. 1), a posterior cut surface (corresponding to surface 2 in FIG. 1), an anterior cut surface (corresponding to surface 3 in FIG. 1), an anterior chamfer cut surface (corresponding to surface 4 in FIG. 1) and a posterior chamfer cut surface (corresponding to surface 5 in FIG. 1). These cuts are typically made with oscillating saw blades.

A number of different devices can be used to control the positioning of the saw blades. Flat metallic blocks on which the saw blade is rested, obviously rely to some extent on the skill of the surgeon to avoid tilting of the saw blade, as may happen when the saw encounters a localized harder (sclerotic) section of bone, or when the saw blade has a long travel beyond the guide surface. Slots having small clearance relative to the thickness of the saw blade may also be used. In general these offer better control of the saw blade than open style blocks.

Block type cutting guides are shown in U.S. Pat. Nos. 4,474,177, 4,487,203, 4,502,483, 4,524,766 and 4,567,885.

Fulcrum type cutting guides are described in U.S. Pat. No. 4,718,413 and also in U.S. Pat. No. 4,892,093. These consist of an upper and a lower guide surface which are linearly separated along the plane of intended cut by the saw blade. By providing a separation between the two surfaces the saw blade, including its tooth set, may be introduced between the two surfaces and then biased against them to control the cutting plane.

The separation of the guide surfaces normal to the plane of operation of the saw blade is typically matched to the thickness of the saw blade. The choice of orientation of the guide surfaces is chosen so that any deviation by the surgeon in maintenance of the contact between the saw blades and either of the guide surfaces results in conservative removal of bone, which may be subsequently corrected. The guide of U.S. Pat. No. 4,892,093 sits on the already prepared distal femur and provides for the cutting of four additional cuts.

The femoral components may be located with six degrees of freedom relative to the patient's femoral geometry. These can be expressed in a Cartesian manner relative to orthogonal anatomical reference planes as shown in FIG. 2. Angulation: Varus-Valgus, Flexion-Extension and Internal-External Rotation. Linear Position: Inferior-Superior, Anterior-Posterior and Medial-Lateral. To position the component on the bone, a number of datum features of the patients anatomy and their relative location as controlled by soft tissue structures at the knee may be utilized.

Two major schools of thought exist as to the optimum method to provide consistent functional placement. The first is independent femoral anatomical placement. In this technique the femoral component is positioned on the femur by referencing datum features on the femur itself. The second is referenced to the tibial position. In this technique the position of the femoral component is controlled relative to the proximal cut of the tibia. The ligaments and other soft tissue structures at the knee joint will in this case affect the femoral component's position. The positional referencing, according to different methodologies, is performed surgically prior to placing the femoral component.

A third technique is varus-valgus and flexion-extension. Angulation of the component in planes is usually performed simultaneously. The reference datum is either the femoral shaft or the line joining the center of the knee and the hip joints. Two major techniques for accomplishing this are currently used. First is intramedullary alignment. A rod is introduced through the center of the knee into the intramedullary space and passed up the inside of the femur to the internal isthmus, establishing an instrument axis within the femoral shaft (medullary canal of the femur). This technique has been found to be very reliable. The second is extramedullary alignment. An external guide rod is aligned with the anterior cortex of the femur, or from the center of the knee to the femoral head.

Current techniques generally require the sequential use of alignment and cutting guides. In most current systems multiple cutting guides are needed to fully prepare the distal femur for the implant. Because these sequential operations require the assembly and disassembly of instrument configurations and the use of intermediate data cut onto the bone, there are penalties in terms of time of surgery and accuracy.

U.S. Pat. No. 5,454,816 discloses an orthopedic instrument for guiding a saw blade for shaping the distal end of a human femur to receive an endoprosthetic femoral component. The instrument includes a base component provided with a guide for guiding cutting elements for shaping all of the necessary surfaces to receive the femoral component to be fitted once the base component is fitted to the bone. Also included are alignment elements for aligning the base component on the bone and elements for attaching the base component to the bone after alignment.

All of the prior art cutting guides have certain drawbacks. These include the inability to provide accurate cuts on a variety of different size femurs, inability to accurately align with one or more of the femoral axes, difficulty in fixation of the guide to the femur, inability to make adjustments in positioning after alignment tools are removed, impingement of soft tissue when securing the cutting guide, etc.

SUMMARY OF THE INVENTION

It is therefore an object of the invention to provide methods and tools for performing femoral resection.

It is also an object of the invention to provide tools for performing femoral resection which maintain proper alignment while multiple resection cuts are made.

It is another object of the invention to provide methods for performing femoral resection in which a minimum number of tools are used.

It is still another object of the invention to provide methods and tools which enhance the accuracy of femoral resection.

It is also an object of the invention to provide methods and tools for performing femoral resection on a variety of different size femurs.

It is another object of the invention to provide methods and tools for performing femoral resection which allow for intraoperative adjustment of the cutting guide position.

It is still another object of the invention to provide tools for performing femoral resection which are easy to attach to the femur with minimal soft tissue impingement.

In accordance with these objects which will be discussed in detail below, the invention contemplates a tool set, including a plurality of different size cutting blocks (also referred to herein as "cutting guides"); and methods for resecting the distal femur prior to implanting a prosthetic femoral component.

The cutting guides of the present invention, according to preferred embodiments thereof, each include (a) a block having a plurality of guiding surfaces, the plurality of guiding surfaces including (a1) an anterior cutting guide surface for resecting the anterior cortex of the femur; (a2) a posterior cutting guide surface for resecting the posterior condyles; (a3) an anterior chamfer cutting guide surface; (a4) a posterior chamfer cutting guide surface; (a5) a distal cutting guide surface for resecting the distal end of the femur; and (b) means for securing the block to the distal femur.

The femoral resection tools of the present invention include a posterior condyle alignment guide, an IM rod with an adjustable valgus bushing assembly, zero, three, and five degree, left and right external rotation plates, an anterior sizing boom having a stylus and a pair of medial/lateral drill guides, a plurality of self-tapping screws, 0 mm, 2 mm and 4 mm proximal positioning fixtures with optional 2mm anterior and posterior positioning fixtures, and a plurality of different size cutting guide blocks (the aforementioned "cutting guides"), each adapted to fit over the proximal positioning fixtures.

As indicated hereinabove, the cutting guide blocks contemplated by the preferred embodiment of the invention, provide three point cutting blade contact for guiding the anterior resection, posterior resection, posterior chamfer, anterior chamfer, and distal resection.

According to the methods of the invention, the valgus bushing is attached to the appropriate external rotation guide plate and both are attached to the posterior condyle alignment guide. An access hole is drilled into the IM canal. The IM rod is inserted through the valgus bushing and in the IM canal so that the assembly rests against the distal and posterior surfaces of the femur.

The assembly is locked securely into position and the anterior sizing boom is attached to the assembly. The stylus of the sizing boom is moved into position over the anterior femur and a size is indicated by indicia on a vertical post of the sizing boom.

The medial/lateral drill guides are moved against the medial and lateral sides of the femur and one or two fixation pins (self-tapping screws), depending on desired stability, are inserted through the holes in each drill guide. The drill guides, sizing boom, and alignment assembly are all removed leaving only the four fixation pins.

A pair of proximal positioning fixtures are selected and slid onto the fixation pins.

According to an alternate embodiment of the invention a pair of modular positioning fixtures can be detachably attached to the extension arms ahead of time to form an integrated drill guide assembly. According to the alternate embodiment of the invention, the need to select and slide a pair of positioning fixtures onto the fixation pins would be eliminated.

An appropriately sized cutting block is selected, based on the size indicated by the sizing boom, and is slid onto the proximal positioning fixtures. Additional fixation pins may then used to secure the position of the cutting block.

With the cutting block in place, five resections may be performed preferably in the following order: anterior resection, posterior resection, posterior chamfer, anterior chamfer, and distal resection. The rational behind this sequence is to allow the surgeon the ability to change the size and/or position of the femur immediately following the resection of the anterior femur.

The methods and tools of the invention provide for a wide range of alignment and sizing of the cutting guides described herein.

The cutting guides contemplated by the invention provide for very accurate cuts. The proximal positioning fixtures allow for 0 mm, 2 mm, or 4 mm distal offset and further, according to a presently preferred embodiment, also optionally permits +/-2 mm anterior/posterior offset to correct any mistakes made in the initial sizing of the femur. The cutting blocks contemplated by the invention also allow for medial-lateral positioning. All of these positioning steps can be carried out between cuts thereby allowing intraoperative adjustment of the position of a cutting block.

The invention provides all of the advantages of anterior referencing without the disadvantage of flexion gap anterior-posterior sizing mismatch.

Additional objects and advantages of the invention will become apparent to those skilled in the art upon reference to the detailed description taken in conjunction with the provided figures.

DETAILED DESCRIPTION

Turning now to FIGS. 3–12, the methods and tools of the invention will be described in detail with reference to the order in which the tools are used in performing the methods of the invention.

Figure 1:
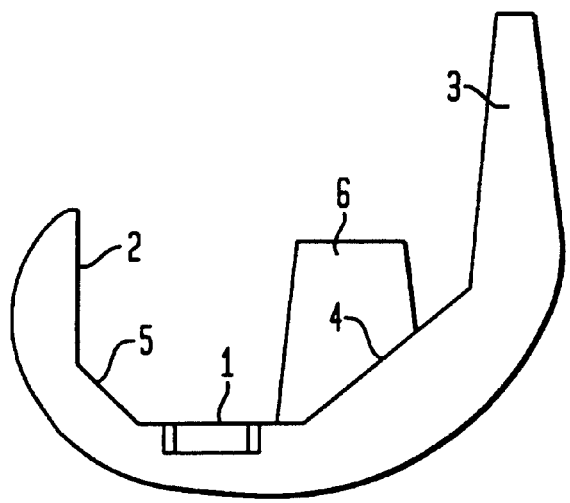
FIG. 1 is a sectional view of a prior art femoral component.
Figure 2:
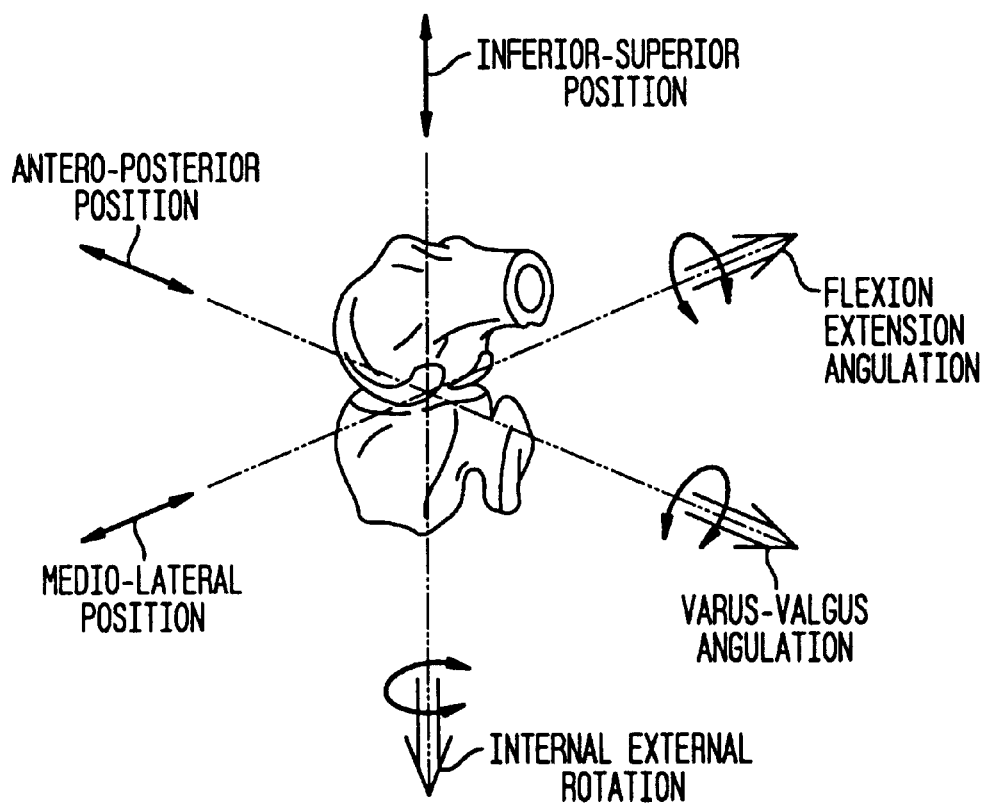
FIG. 2 is a diagram showing the various reference directions for a knee.
Figure 3:
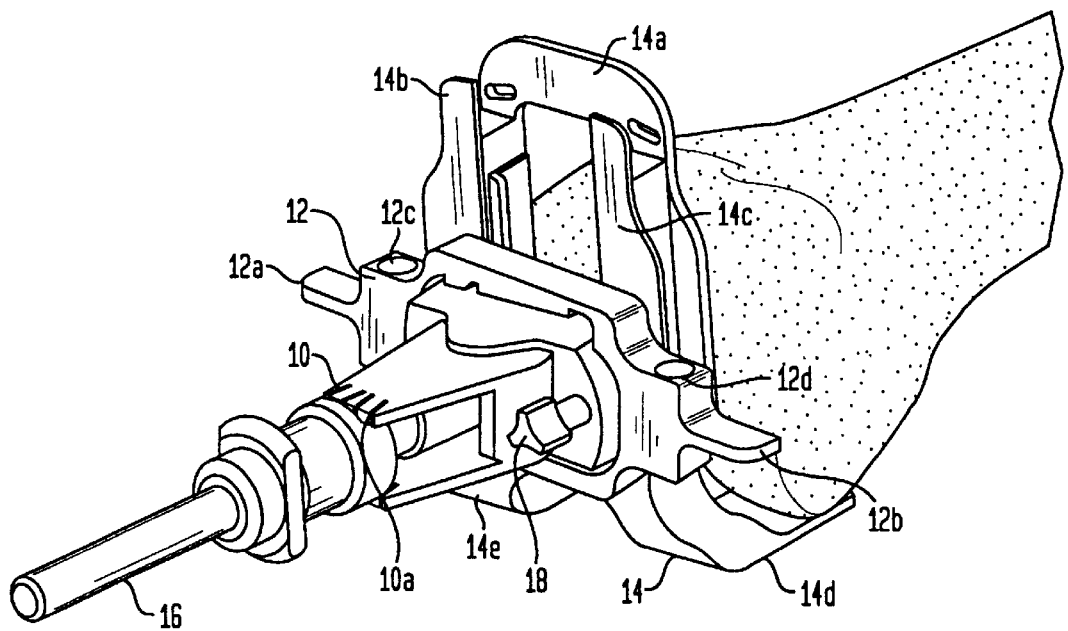
FIG. 3 is a perspective view of the IM rod, valgus bushing, external rotation guide, and posterior alignment guide attached to a distal femur.

As shown in FIG. 3, after the IM canal of the femur has been drilled by known methods, the valgus bushing 10 is attached to the appropriate external rotation guide plate 12 and both are attached to the posterior condyle alignment guide 14. The IM rod 16 is inserted through the valgus bushing 10 and in the IM canal so that the assembly rests against the distal and posterior surfaces of the femur. The assembly is locked securely into position with the locking knob 18.

According to one embodiment of the invention, the valgus bushing 10 allows the IM rod to pivot up to 9 degrees left or right and indicia 10a on the bushing indicate the angle of the pivot.

Further, according to a preferred embodiment of the invention, several different external rotation guides are provided, namely, three degrees left, three degrees right, three degrees left, five degrees right, and zero degrees (neutral) rotation. Each of the rotation guides is provided with a pair of wings 12a, 12b for visual reference to the transepicondylar axis; and a pair of vertical bores 12c, 12d. The posterior alignment guide 14 has a vertical portion 14a which rests against the distal end of the femur, two vertical arms 14b, 14c which are spaced apart from the vertical portion 14a and which are pressed against by the rotation guide 12 and a pair of horizontal feet 14d, 14e which rest against the posterior condyles of the femur.

Figure 4:
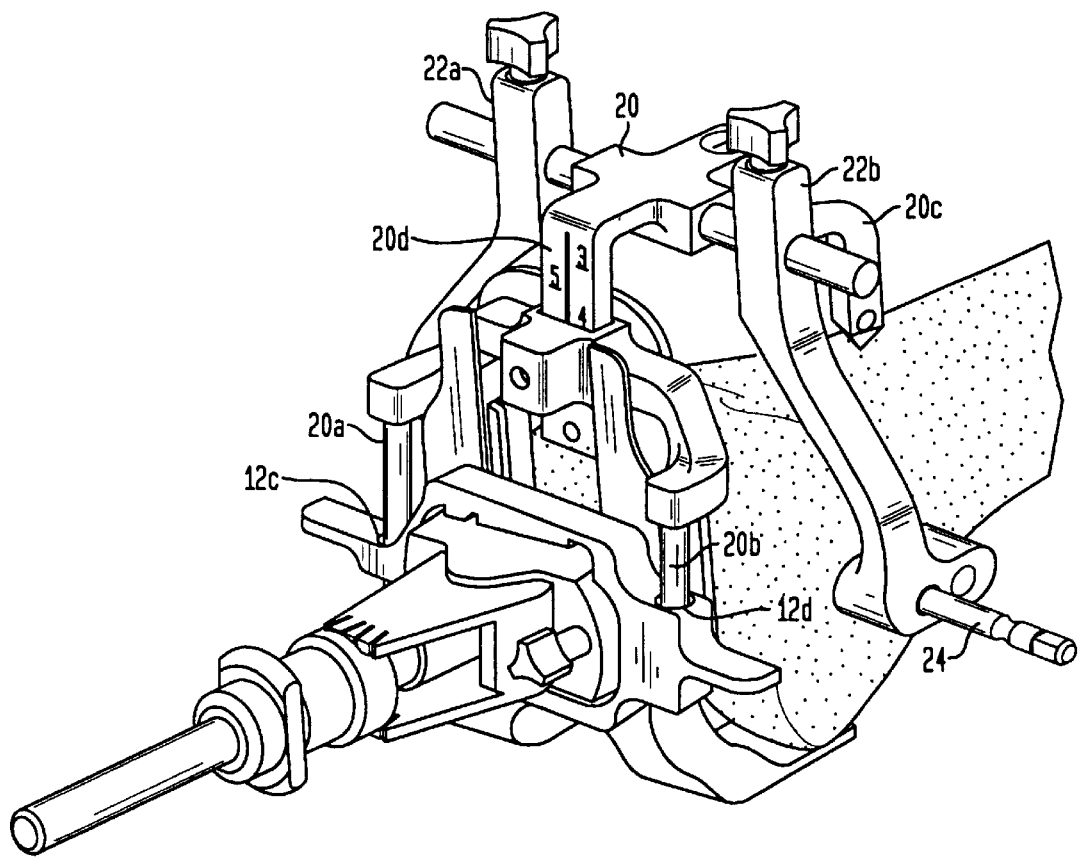
FIG. 4 is a perspective view showing the anterior sizing boom and detachable drill guides attached to the assembly.
Figure 5:
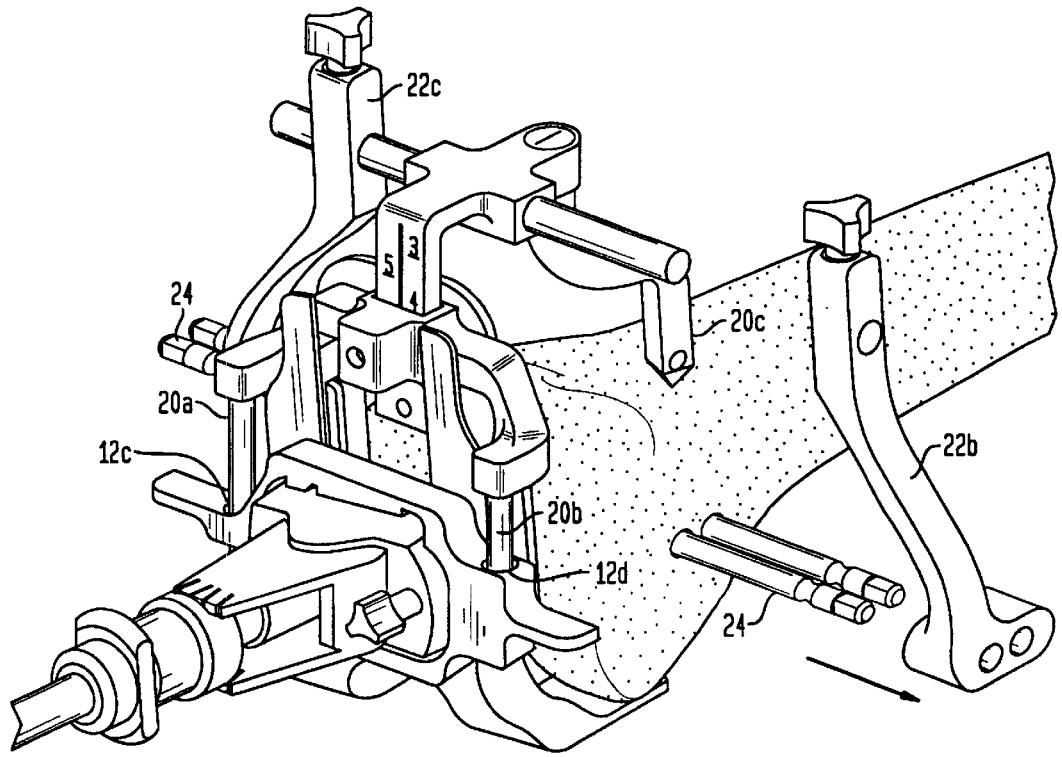
FIG. 5 is a perspective view showing the fixation pins installed and one of the detachable drill guides removed.

Turning now to FIGS. 4 and 5, after the alignment assembly (including the guide plate 12 and the posterior alignment guide 14) is attached as described above, the anterior sizing boom 20 is attached to the assembly. The sizing boom has a pair of spaced apart vertical posts 20a, 20b which engage the bores 12c, 12d in the rotation guide. When so engaged, the sizing boom 20 rests on top of the alignment guide 14. The sizing boom 20 is also provided with a vertically movable stylus 20c and sizing indicia 20d which indicate the relative position of the stylus 20c. A pair of drill guides 22a, 22b are removably attachable to the top of the boom 20. The drill guides include positional fixtures or diodes 26 removably attached to the lower end.

After the boom 20 is attached to the rotation guide 12, the stylus 20c of the sizing boom is moved into position over the anterior femur as illustrated in FIG. 4. The practitioner can locate the stylus on a region at the medial base of the most prominent aspect of the anterior lateral cortex. A size is indicated by indicia 20d. This size can be used to select the appropriate cutting block as described below with reference to FIGS. 7 et seq.

The medial/lateral drill guides 22a, 22b can now be moved against the medial and lateral sides of the femur and locked in place. Fixation pins 24 (self-tapping screws as shown in the illustration), can now be inserted through the holes of the positional fixtures 26 and tapped into the sides of the femur.

The drill guides can then be detached leaving the positional fixtures affixed to the medial and lateral sides of the femur. The sizing boom, drill guides and alignment guide assembly may now all be removed leaving only the four fixation pins 24 and two positional fixtures 26 according to one embodiment of the invention. Preferably, the signing boom drill guides, and alignment assembly are removed one at a time to avoid strain on the fixation pins.

It should be recalled that according to an alternate embodiment of the invention a pair of modular positioning fixtures ("diodes") are detachably attached to the drill guides 22a, 22b ahead of time to form an integrated drill guide assembly. Thus, after the fixation pins are attached, the drill guides may be detached from positioning fixtures 26, leaving the fixtures appropriately positioned on the femur. These positioned fixtures are neutral, since they don not provide for any offset in any direction. According to this alternate embodiment of the invention, the need to select and initially slide a pair of positioning fixtures onto the fixation pins would be eliminated.

Figure 6:
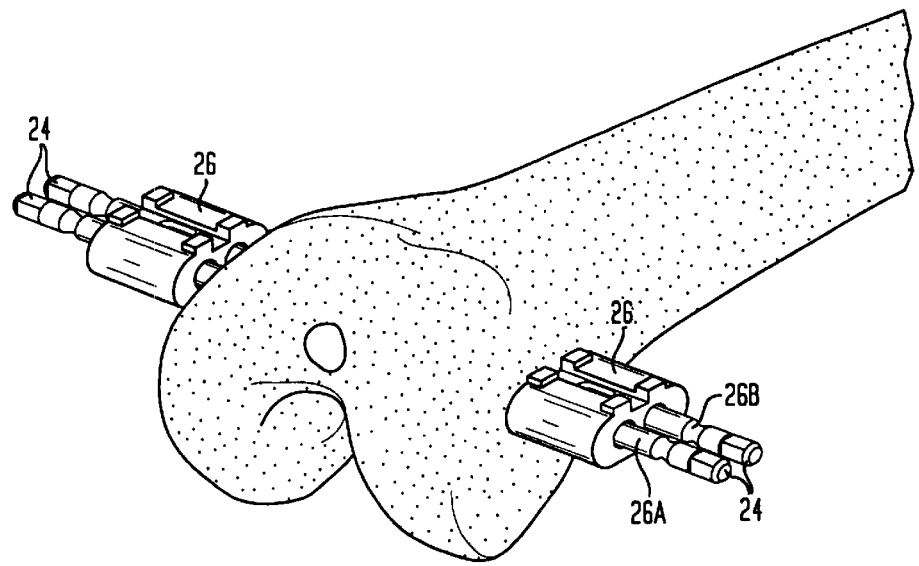
FIG. 6 is a perspective view showing the proximal positioning fixtures installed on the fixation pins.
Figure 7:
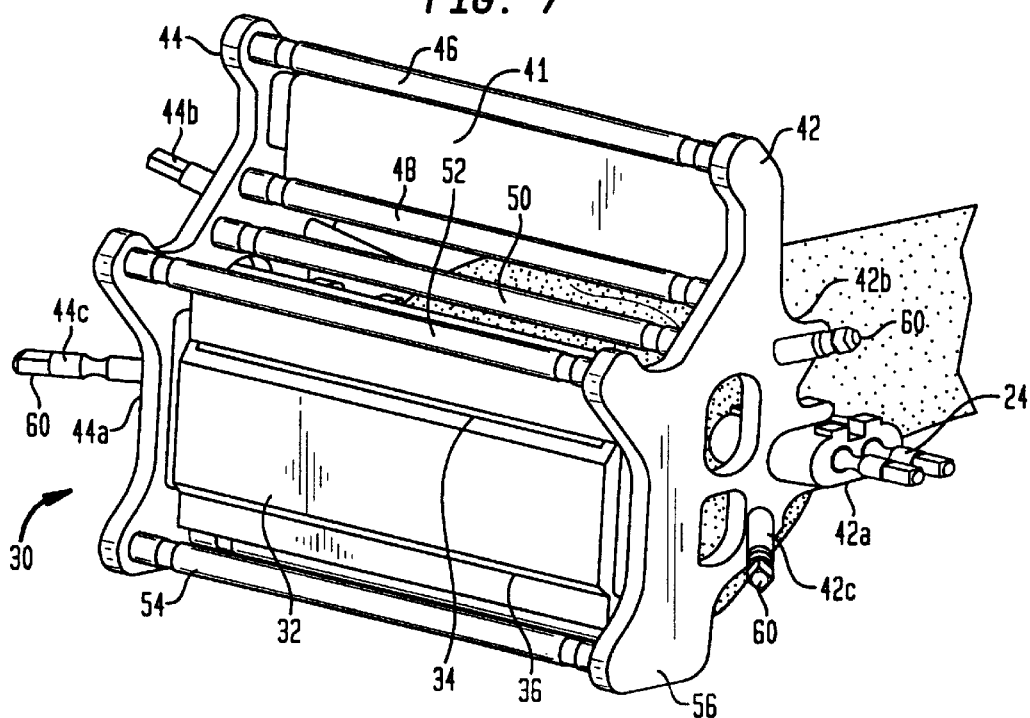
FIG. 7 is a perspective view showing a cutting block installed over the positioning fixtures.

Referring now to FIG. 6, after the fixation pins are installed and the rest of the instrumentation alignment apparatus is removed, the practitioner may select another pair of positioning fixtures 26 that best suits the desired positional alignment of the femoral component. Thus, rather than using the neutral positioning fixtures, the practitioner may remove the neutral positioning fixtures and use offset positioning fixtures, if appropriate . Each positioning fixture has two bores 26a, 26b. The bores are preferably spaced apart from each other by the same distance as the bores in the drill guide so that the fixtures 26 fit over the fixation pins 24 as shown in FIG. 6. They are easily inserted and removed by the practitioner.

According to one embodiment of the invention, different offset positioning fixtures are provided wherein the location of the bores 26a, 26b relative to the outer surface of the positioning fixture varies. Different modular offset positioning fixtures as integrated parts of a drill guide assembly (i.e., modular positioning fixture s attached to the drill guides, for example via a quick release mechanism) are, as indicated contemplated by an alternative embodiment of the invention.

Further, according to one embodiment of the invention, the difference in location of the bores relative to the outer surface of the offset positional fixtures is only proximal-distal. E.g., 0 mm, 2 mm, 4 mm and 6 mm offset positioning fixtures are provided which will vary the proximal-distal location of the cutting block when it is placed over the offset positioning fixtures as described below with reference to FIG. 7. The 0 mm fixture will provide a 8 mm initial resection. The 2 mm fixture will provide a 10 mm resection; and the 4 mm fixture will provide a 12 mm resection.

According to another embodiment of the invention, +/2 mm offset positioning fixtures are provided which will offset the anterior-posterior location of the cutting block when it is placed over the offset positioning fixtures as opposed to the neutral positioning fixtures. According to a preferred aspect of the invention, the positioning fixtures can be interchanged intraoperatively to make adjustments to the resected planes after the initial resection(s) with the neutral positioning fixtures.

Turning now to FIGS. 7–12, after a pair of proximal offset positioning fixtures are selected and slid onto the fixation pins (referring to this one embodiment of the invention for the sake of illustration only), an appropriately sized cutting block 30 may be selected, based on the size indicated by the sizing boom. The cutting block 30 includes a central block member 32 having two chamfer cut slots 34, 36, an upper guiding surface 38, a lower guiding surface 40, a vertical guiding surface 41, and two end plates 42, 44.

Six guiding rods 46, 48, 50, 52, 54, 56 extend between the end plates 42, 44. Each end plate has a slot 42a, 44a for receiving a respective positioning fixture and a plurality of bores 42b, 42c, 44b, 44c for receiving fixation pins 60.

After the cutting block 30 is slid onto the proximal offset positioning fixtures 26, its medial-lateral location is adjusted by visual inspection. Note that osteophyte removal and patella resection may be required in obese patients in which femoral exposure is limited. Additional fixation pins 60 (self-tapping screws) may be used next to secure the position of the cutting block 30. As mentioned above, the cutting block is provided with four bores for fixation pins.

According to the preferred method of the invention, using one screw is acceptable for each side, e.g. lateral posterior and medial anterior. This minimizes soft tissue (patella tendon) interference and allows the intraoperative repositioning of the cutting block using the other two bores without drilling screws close to the previous holes. With the cutting block in place, five resections may be performed, preferably in the following order: anterior resection, posterior resection, posterior chamfer, anterior chamfer, and distal resection.

Figure 8:
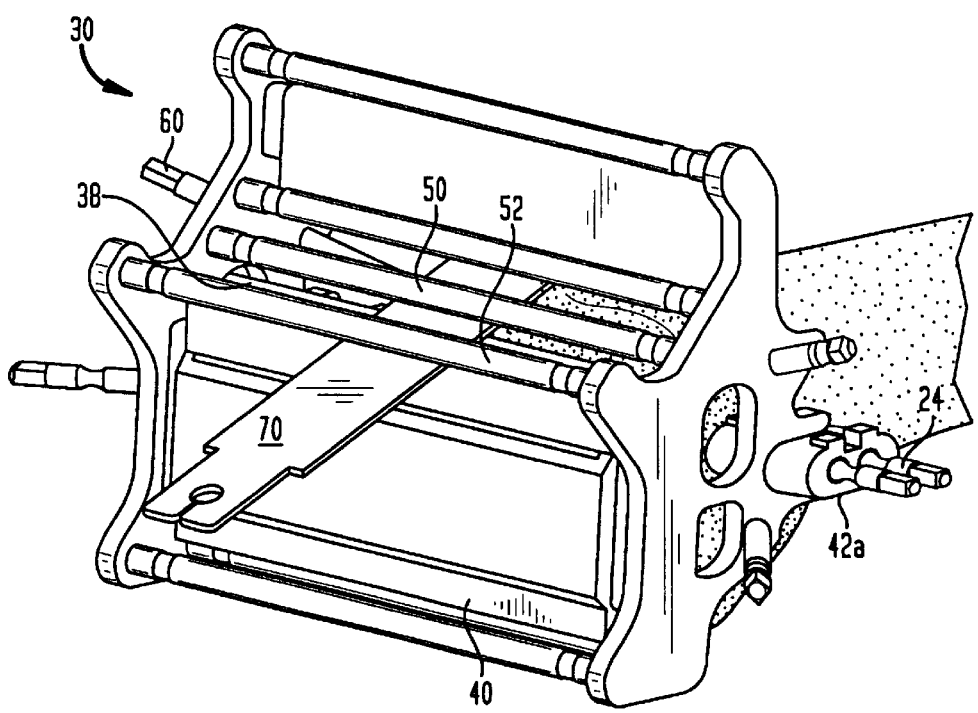
FIG. 8 is a perspective view illustrating the anterior resection of the femur.

FIG. 8 illustrates the anterior resection cut wherein the cutting blade 70 is guided by the top surface 38 and the two bars 50, 52 of the cutting block 30. Thus, a three point cutting guide is provided for this cut.

Figure 9:
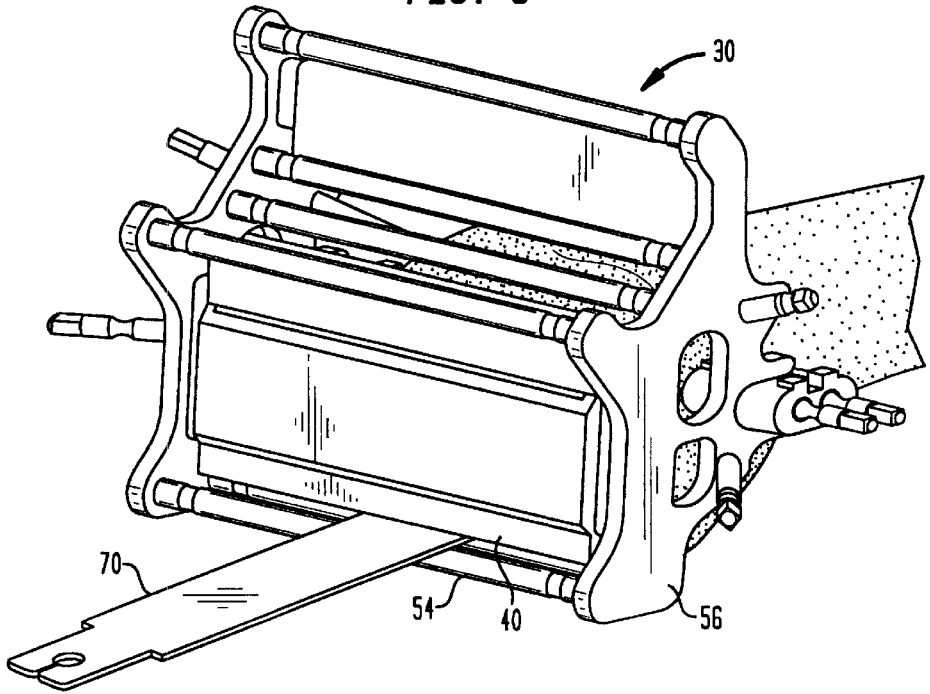
FIG. 9 is a perspective view illustrating the posterior resection of the femur.

FIG. 9 illustrates the posterior resection cut wherein the cutting blade 70 is guided by the bottom surface 40 and the two bars 54, 56 of the cutting block 30. Thus, a three point cutting guide is provided for this cut.

Figure 10:
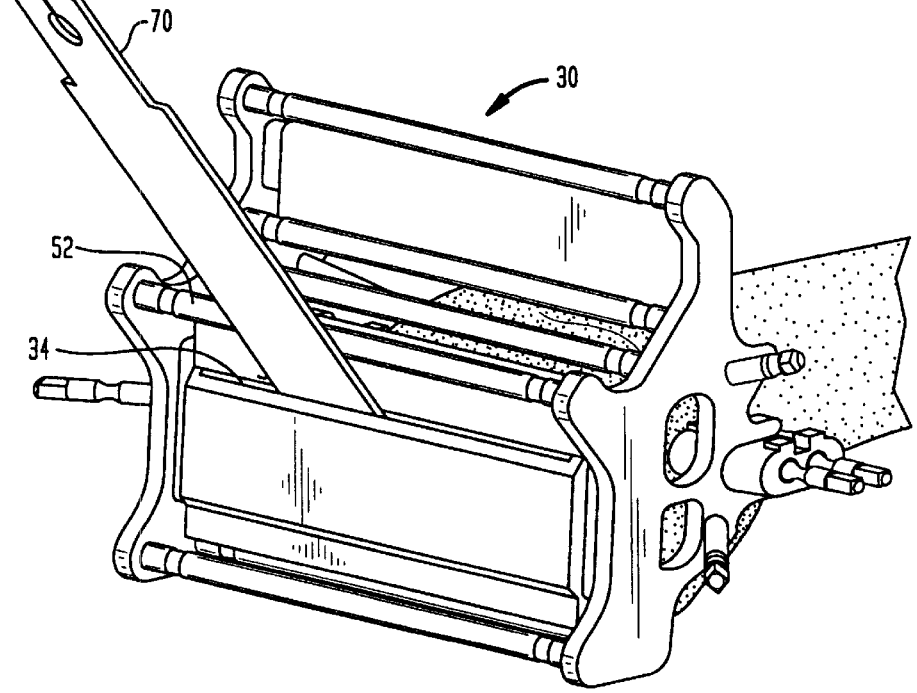
FIG. 10 is a perspective view illustrating the posterior chamfer cut.

FIG. 10 illustrates the posterior chamfer resection wherein the cutting blade 70 is guided by the two surfaces defining slot 34 and bar 52 of the cutting block 30. Thus, a three point cutting guide is provided for this cut.

Figure 11:
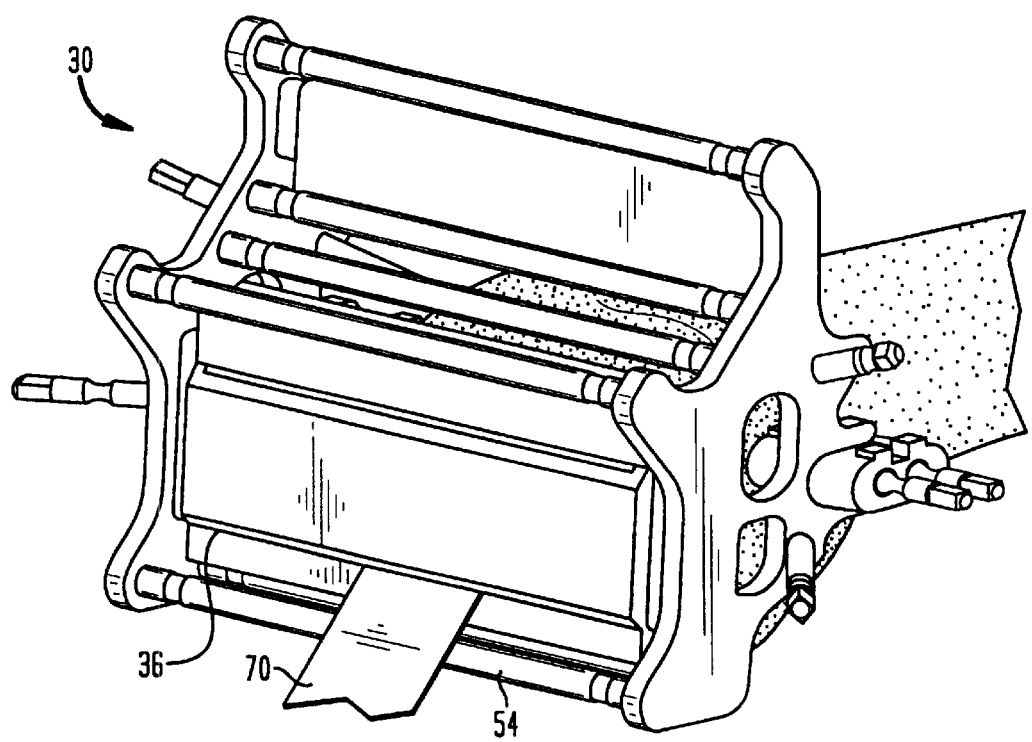
FIG. 11 is a perspective view illustrating the anterior chamfer cut.

FIG. 11 illustrates the anterior chamfer resection wherein the cutting blade 70 is guided by the two surfaces defining slot 36 and bar 54 of the cutting block 30. Thus, a three point cutting guide is provided for this cut.

Figure 12:
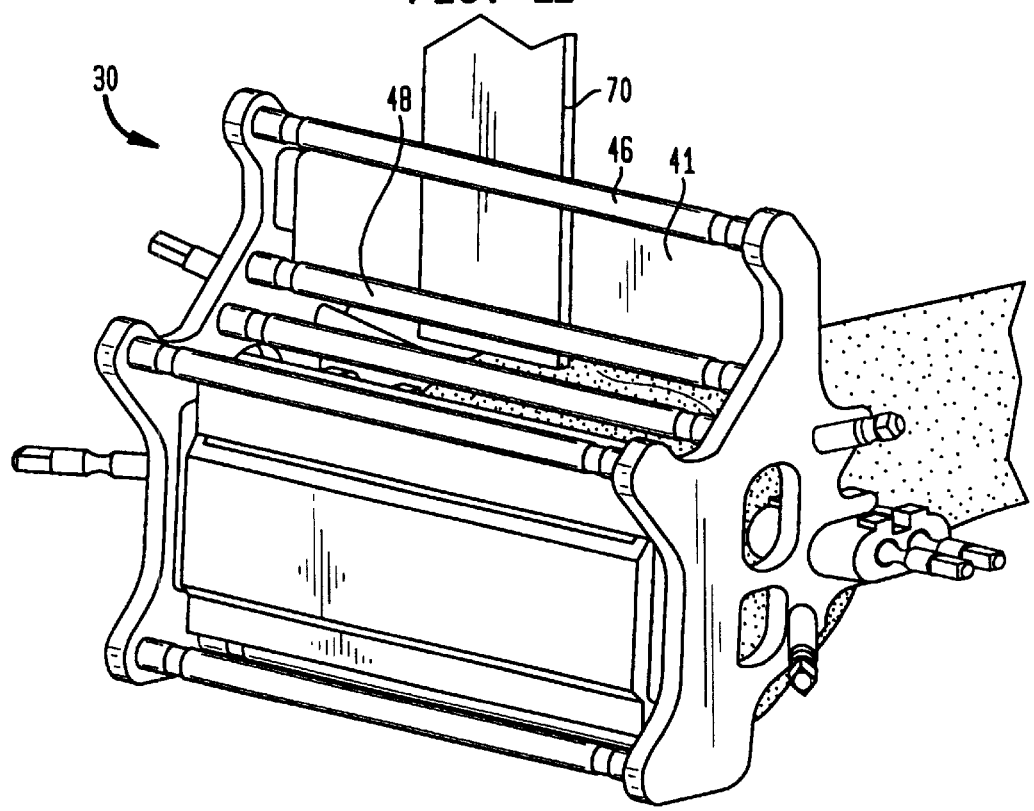
FIG. 12 is a perspective view illustrating the distal resection of the femur.

FIG. 12 illustrates the distal resection cut wherein the cutting blade 70 is guided by the vertical surface 41 and the two bars 46, 48 of the cutting block 30. Thus, a three point cutting guide is provided for this cut.

After all five resection cuts are completed, the cutting block may be removed and the resected surfaces can be examined. Additional resections may be performed using different positioning fixtures to fine tune the operation. When all resections are complete, the cutting block, positioning fixtures, and fixation screws are removed.

The methods and tools of the invention provide for a wide range of alignment and sizing of the cutting guide. The cutting guides contemplated by the invention provide for very accurate cuts since metal-to-metal surfaces are eliminated thus allowing the resultant slot to be tighter toleranced. The proximal positioning fixtures allow for 0 mm, 2 mm, or 4 mm distal offset and further, according to a presently preferred embodiment, also permit +/-2 mm anterior/posterior offset to correct any mistakes made in the initial sizing of the femur. The cutting blocks contemplated by the invention also allow for medial-lateral positioning. All of these positioning steps can be carried out between cuts thereby allowing intraoperative adjustment of the position of the cutting block. The invention provides all of the advantages of anterior referencing without the disadvantage of flexion gap anterior-posterior sizing mismatch.

There have been described and illustrated herein methods and tools for resection of the distal femur. While particular embodiments of the invention have been described, it is not intended that the invention be limited thereto, as it is intended that the invention be as broad in scope as the art will allow and that the specification be read likewise. For example, those skilled in the art will readily appreciate that it is not necessary to be constrained by the preferred embodiment choices of offsets, correction factors, etc., these being application design choices for the tools and cutting guides per se.

It will therefore be appreciated by those skilled in the art that yet other modifications could be made to the provided invention without deviating from its spirit and scope as so claimed.

What is claimed is:

1. An instrument for resecting the distal femur, comprising:

a plurality of cutting guide blocks;

a pair of neutral positioning fixtures, for positioning any one of said cutting guide blocks on the distal femur;

a plurality of offset positioning fixtures for positioning any one of said cutting guide block at an offset position;

an alignment assembly for positioning said pair of positioning fixtures, said alignment assembly including an IM rod, a valgus bushing, a posterior alignment guide for locating an anterior-posterior location of said positioning fixtures, and a plurality of external rotation guides for providing an external rotation; and a drill guide cooperating with said alignment assembly for drilling holes in the distal femur for attaching said pair of positioning fixtures to the distal femur.

2. An instrument according to claim 1, wherein said plurality of external rotation guides includes an external rotation guide providing 3 degrees left external rotation, an external rotation guide providing 3 degrees right external rotation, an external rotation guide providing 5 degrees left external rotation, an external rotation guide providing 5 degrees right external rotation and an external rotation guide providing zero degrees rotation.

3. An instrument according to claim 2, wherein said posterior alignment guide includes:

a vertical portion for abutting the distal end of the femur; and a pair of feet for abutting the posterior condyles of the distal femur, wherein said alignment assembly is assembled by selecting an appropriate external rotation guide from said plurality of external rotation guides, attaching said appropriate external rotation guide to said valgus bushing, inserting said IM rod through said valgus bushing, said appropriate external rotation guide and said posterior alignment guide and inserting said IM rod into the IM canal of the femur until said alignment assembly abuts the distal end of the femur.

4. An instrument according to claim 1, comprising a sizing boom cooperable with said external rotation guide and said posterior alignment guide for selecting said one cutting guide block from said plurality of cutting guides.

5. An instrument according to claim 4, wherein said sizing boom includes posts for attaching to said external rotation guide and a vertically adjustable stylus for contacting the most prominent aspect of the anterior lateral cortex to determine the appropriate size for said one cutting guide.

6. An instrument according to claim 5, wherein said pair of positioning fixtures are removably attached to one end of said drill guide and another end of said drill guide is removably attached to said sizing boom.

7. An instrument according to claim 6 further comprising self tapping pins for attaching said pair of positioning fixtures to the distal femur.

8. An instrument according to claim 1, wherein each of said plurality of external rotation guides comprises a pair of tabs for visually peferencing the position of said external rotation guide with respect to the posterior condyles.

9. An instrument for positioning a cutting guide on the distal femur, comprising:
    an alignment assembly including:
        an IM rod for inserting into the IM canal;
        a valgus bushing attached to said IM rod;
        an external rotation guide for providing an external rotation, said external rotation guide attached to said valgus bushing; and
        a posterior alignment guide attached to said external rotation guide and abutting the posterior condyles of the distal femur;
    a drill guide cooperable with said alignment assembly;
    a pair of neutral positioning fixtures for receiving the cutting block on the distal femur at a neutral position, said neutral positioning fixtures being removably attached to said drill guide and attachable to the medial and lateral sides of the femur, wherein when said alignment assembly is assembled on the distal femur and said drill guide cooperates with said alignment assembly so as to position said neutral positioning fixtures on the medial and lateral sides of the femur; and
    a plurality of pairs of offset positioning fixtures for receiving the cutting block of the distal femur at an offset orientation, each of said plurality pairs of offset positioning fixtures being attachable to the medial and lateral sides of the femur.

10. An instrument according to claim 9, comprising self tapping pins for attaching said pair of neutral positioning fixtures to the medial and lateral sides of the femur.

11. An instrument according to claim 10, wherein each of said plurality pairs of offset positioning fixtures may be attached to the medial and lateral sides of the femur via said self tapping pins.

12. An instrument according to claim 10, wherein said plurality of offset positioning fixtures includes at least one proximal-distal offset positioning fixture for receiving the cutting block at an orientation offset proximally/distally from the neutral position.

13. An instrument according to claim 12, wherein said at least one proximal-distal offset positioning fixture includes an offset positioning fixture for receiving the cutting block 2 mm offset from the neutral position, an offset positioning fixture for receiving the cutting block 4 mm offset from the neutral position, and an offset positioning fixture for receiving the cutting block 6 mm offset from the neutral position.

14. An instrument according to claim 10, wherein said plurality of offset positioning fixtures includes at least one anterior-posterior offset positioning fixture for receiving the cutting block at an orientation offset anteriorally/posteriorally from the neutral position.

15. An instrument according to claim 14, wherein said at least one anterior-posterior offset positioning fixture includes an anterior-posterior offset positioning fixture for receiving the cutting block at an orientation offset anteriorally/posteriorally from the neutral to a value selected from the range of about −2 mm to about +2 mm.

16. An instrument for resecting the distal femur, comprising:
    a plurality of cutting guide blocks, each of said plurality of cutting guide blocks having anterior cutting guide surface defining three points, a posterior cutting guide surface defining three points, an anterior chamfer guide surface defining three points, a posterior chamfer guide surface defining three points and a distal cutting guide surface defining three points;
    a pair of positioning fixtures, for positioning one of said cutting guide blocks on the distal femur;
    an alignment assembly for positioning said pair of positioning fixtures; and
    a drill guide cooperating with said alignment assembly for drilling holes in the distal femur for attaching said pair of positioning fixtures to the distal femur;
    a sizing boom attachable to said alignment assembly for selecting said one cutting guide block from said plurality of cutting guides, said sizing boom including an adjustable stylus for contacting the most prominent aspect of the anterior lateral cortex to determine the appropriate size for said one cutting guide.

17. An instrument according to claim 16, wherein each of said three points includes at least one rod.

18. An instrument according to claim 17, wherein each of said three points includes at least one planar surface.

19. An instrument according to claim 16, wherein each of said three points includes at least one planar surface.

20. An instrument according to claim 19, wherein each of said three points includes at least one rod.

21. An instrument according to claim 16, wherein said alignment assembly comprises an IM rod, a valgus bushing, a posterior alignment guide for locating an anterior-posterior location of said positioning fixtures, and a plurality of external rotation guides for providing an external rotation.

22. A method for resecting the distal femur, comprising the steps of:
    locating an appropriate position for a cutting guide block on the distal femur;
    determining an appropriate size cutting guide block;
    removably attaching positioning fixtures to the distal femur at the appropriate position;
    removably attaching the appropriate size cutting guide block to the positioning fixtures;
    resecting the femur using a saw and the appropriate cutting guide block;
    removing the appropriate size cutting guide block;
    removably reattaching the appropriate size cutting guide block at an offset orientation; and
    further resecting the femur.

23. A method according to claim 22, wherein the step of locating further includes:

selecting an appropriate external rotation guide from a plurality of external rotation guides;

attaching the appropriate external rotation guide to a valgus bushing;

forming an alignment assembly by inserting an IM rod through the valgus bushing, external rotation guide and a posterior alignment guide;

inserting the IM rod into the IM canal until the alignment assembly abuts the distal femur; and attaching a drill guide including the positioning fixtures to the alignment assembly, wherein the positioning fixtures are located at the appropriate position.

24. A method according to claim 23, wherein said step of determining further includes:

attaching a sizing boom including a stylus and sizing indicia to the alignment assembly;

rotating the stylus until it contacts the anterior femur; and reading the sizing indicia to determine the appropriate size for the cutting block.

25. A method according to claim 23, wherein the plurality of external rotation guides includes an external rotation guide providing 3 degrees left external rotation, an external rotation guide providing 3 degrees right external rotation, an external rotation guide providing 5 degrees left external rotation, an external rotation guide providing 5 degrees right external rotation and an external rotation guide providing zero degrees rotation.

26. A method according to claim 25, wherein said step of selecting further includes selecting offset positioning fixtures to offset the orientation of the cutting block proximally/distally.

27. A method according to claim 26, wherein the plurality of offset positioning fixtures includes an offset positioning fixture for offsetting the cutting block 2 mm proximally, an offset positioning fixture for offsetting the cutting block 4 mm proximally, and an offset positioning fixture for offsetting the cutting block 6 mm proximally.

28. A method according to claim 25, wherein said step of selecting further includes selecting offset positioning fixtures to offset the orientation of the cutting block anteriorally/posteriorally.

29. A method according to claim 28, wherein the plurality of offset positioning fixture includes an offset positioning fixture for offsetting the cutting block anteriorally/posteriorally to a value selected from the range of about −2 mm to about +2 mm.

30. A method according to claim 22, wherein said step of removably reattaching the cutting guide block further includes the steps of:

determining the offset orientation;

selecting offset positioning fixtures from a plurality of offset positioning fixtures;

removably attaching offset positioning fixtures to the femur; and the step of removably reattaching the cutting guide block further includes removably attaching the cutting guide block to the offset positioning fixtures to position the cutting guide at the offset orientation.

31. A method according to claim 22, further comprising the step of selecting the appropriate cutting guide blocks from a plurality of cutting guide blocks, each of said plurality of cutting guide blocks having anterior cutting guide surface defining three points, a posterior cutting guide surface defining three points, an anterior chamfer guide surface defining three points, a posterior chamfer guide surface defining three points and a distal cutting guide surface defining three points.

32. A method according to claim 31, wherein said step of resecting further includes the steps of:

resecting the anterior cortex of the femur using a saw placed between the three points of the anterior cutting guide surface;

resecting the posterior condyles of the femur using a saw placed between the three points of the posterior cutting guide surface;

resecting the anterior chamfer of the femur using a saw placed between the three points the anterior chamfer cutting guide surface;

resecting the posterior chamfer of the femur using a saw placed between the three points of the posterior chamfer cutting guide surface; and resecting the distal end of the femur using a saw placed between the three points of the distal cutting guide surface.

* * * * *

UNITED STATES PATENT AND TRADEMARK OFFICE
CERTIFICATE OF CORRECTION

PATENT NO. : 6,558,391 B2
DATED : May 6, 2003
INVENTOR(S) : Stuart L. Axelson, Jr., Michael A. McGovern and Reese K. Meyers It is certified that error appears in the above-identified patent and that said Letters Patent is hereby corrected as shown below:

Column 1,
Line 55, delete ",".

Column 2,
Line 23, "patients" should read -- patient's --.

Column 4,
Line 30, after "then" insert -- be --

Column 6,
Line 28, "don" should read -- do --.
Line 53, after "indicated" insert -- , --.
Line 63, "a" should read -- an --.

Column 7,
Line 11, "o f" should read -- of --.

Column 8,
Line 38, "block" should read -- blocks --.

Column 9,
Line 23, "peferencing' should read -- referencing --.

Column 11,
Line 44, "fixture" should read -- fixtures --.

UNITED STATES PATENT AND TRADEMARK OFFICE
CERTIFICATE OF CORRECTION

PATENT NO.      : 6,558,391 B2
DATED           : May 6, 2003
INVENTOR(S)     : Stuart L. Axelson, Jr., Michael A. McGovern and Reese K. Meyers It is certified that error appears in the above-identified patent and that said Letters Patent is hereby corrected as shown below:

<u>Column 12,</u>
Line 35, after "points" insert -- of --.

Signed and Sealed this

Thirtieth Day of September, 2003

JAMES E. ROGAN
*Director of the United States Patent and Trademark Office*